United States Patent [19]

Tanny

[11] Patent Number: 5,033,479

[45] Date of Patent: Jul. 23, 1991

[54] LASER BEAM RESISTANT MATERIALS

[75] Inventor: Gerald Tanny, Rehovot, Israel

[73] Assignee: Gelman Sciences, Inc., Ann Arbor, Mich.

[21] Appl. No.: 518,218

[22] Filed: May 3, 1990

[51] Int. Cl.⁵ .............................................. A61F 13/00
[52] U.S. Cl. ........................................ 128/849; 606/2; 128/858; 128/846
[58] Field of Search ............................... 128/849–858; 606/1, 2; 604/368–372

[56] References Cited

U.S. PATENT DOCUMENTS

| 4,520,814 | 6/1985 | Weeks | 606/2 |
| 4,601,286 | 7/1986 | Kaufman | 604/368 X |
| 4,715,366 | 12/1987 | Teeple | 128/849 |
| 4,735,623 | 4/1988 | Hatzenbuhler et al. | 604/369 |
| 4,793,003 | 12/1988 | Riedel et al. | 128/858 |
| 4,901,738 | 2/1990 | Brink et al. | 128/849 |

Primary Examiner—Robert A. Hafer
Assistant Examiner—Kerry Owens
Attorney, Agent, or Firm—Krass & Young

[57] ABSTRACT

A method and a system are provided for protecting patients and equipment from the damaging effects of stray laser light emissions. Porous barrier materials are selected to have a pore geometry functionally related to the wavelength of emitted laser so as to cause destructive interference of the light beam when the beam encounters the porous material.

12 Claims, 1 Drawing Sheet

*TEST CARRIED OUT FOR ONLY 30 SECONDS.
NO FAILURE OBSERVED

LASER BEAM RESISTANT MATERIALS

FIELD OF THE INVENTION

The present invention is directed to surgical articles, fabric materials, coverings, apparel, and the like, and more particularly to microporous, laser resistant barrier articles for use as sterile air-permeable bacteria-impermeable items in laser surgery, such as surgical drapes, sponges, padding, gowns, masks, and the like.

The use of surgical lasers offers the medical community distinct advantages in the operating room. Consequently, the use of lasers in the operating room is expected to increase dramatically; lasers could be used in half of all surgeries by the end of the century. Typical lasers used in surgery include neodymium-yttrium-aluminum-garnet (ND-YAG) lasers, argon lasers, and $CO_2$ lasers. As an illustration, ND-YAG lasers operate at a wavelength of $1.06 \times 10^3$ nanometers, i.e., 1.06 microns or $\mu$m. Argon lasers, e.g., operate at wavelengths of 0.4579 and $0.5145 \times 10^3$ nanometers. $CO_2$ lasers operate at a wavelength of $10.6 \times 10^3$ nanometers. Most commercial lasers operate at wavelengths ranging from $0.3 \times 10^3$ nanometers to the wavelength of the ND-YAG laser of $1.06 \times 10^3$ nanometers.

Although laser surgery affords the public improved health care, the use of lasers presents new hazards in the operating room environment. Despite efforts to confine laser beams to the intended operative site, lasers can and inadvertently do sometimes become focused on unintended locations, either as the direct laser beam or as stray light from the beam. This has resulted in burns, permanent eye damage, fires and, in some instances, death. For example, polyvinyl chloride (PVC) is a material frequently used in endotracheal tubes. PVC tubes absorb energy from the laser. Since endotracheal tubes carry mainly oxygen, case histories are known where a laser beam accidently focused on an endotracheal tube has caused an explosion in the patient's throat. Additionally, lasers create potentially hazardous smoke (laser plume) in which viral and carcinogenic components have been identified.

The majority of surgical drapes, gowns, and other operating room apparel fabrics are disposable and are composed of polycellulose or spunbound polypropylene. Unfortunately, the types of these fabrics in use are easily penetrated by the three most common surgical lasers, i.e., $CO_2$, ND-YAG and argon. For example, $CO_2$ lasers penetrate current polycellulosic based fabrics and polypropylene fabrics in less than 0.01 second. ND-YAG lasers penetrate these materials in less than 0.2 second. The polypropylene materials tend to melt away from the laser beam, while the cellulosic materials tend to char around the edge of the beam. Such flammable characteristics have led to laser induced operating room fires and injury where such fabrics have melted into patients.

Further, materials readily burned through by stray laser light lose their sterile barrier function, subjecting the patient to the risk of infection. Cotton towels wetted with sterile saline solution are employed to absorb laser beams, but offer the disadvantage of dripping linty solution into the operative site, and unless the cotton towels are rewetted periodically, these too can ignite.

SUMMARY OF THE INVENTION

The present invention concerns technology for protecting patients and equipment from the damaging effects of direct or stray laser light emissions. The present invention is based on the discovery that barrier articles or materials comprising microporous membranes or films having 1) a thickness and 2) total solid pore-wall structure that are functionally and mutually related to the wavelength of incident laser light can by that fact desirably impede, block, or cause destructive interference of the laser light.

Pursuant to the discovery, the invention in one preferred aspect concerns a protective barrier article for a surgical operation in cooperative employment with an incident axial laser light beam at a chosen wavelength focused on an intended or target operative site. The barrier article comprises a laser-beam resistant polymeric microporous membrane having 1) membrane thickness and 2) total solid membrane pore-wall structure functionally related to said wavelength such that when the membrane is interposed transversely of the beam said thickness and total pore-wall structure cooperatively impede at least about 40% and preferably more than 90% of the light focused as off-target laser beam light and/or stray light from an on-target beam.

Thus when the laser beam or stray laser light encounters the porous barrier material, the laser beam is temporarily made non-coherent and is inhibited from progressing along its path for a significantly greater length of time without appreciable or visible damage to the material or loss of function (as compared to conventional non-porous materials or materials having pore-wall structures which being functionally unrelated to the wavelength of the emitted laser light noticeably lose their barrier function almost instantaneously.).

Advantageously, the protective barrier articles of the invention comprise a microporous membrane which is laser beam resistant and surprisingly can also be gas-permeable and bacteria-impermeable without loss of useful laser light barrier function. The laser beam resistant microporous membranes are especially suitable for surgical coverings such as coverings, drapes, gowns, masks, surgical equipment covers, and the like.

The solid polymeric pore-walls which provide the framework for the individual pores preferably have a diameter or thickness equal to about one-fifth to about one-third of the wavelength of the laser beam encountered by the membrane. For example, for incident laser light having a wavelength of 1.06 microns the diameter or thickness should be about 0.2 to about 0.3 microns. It has been observed that pore-walls with thickness in this range restrict the passage of the incident beam, while at the same time resisting destruction by the beam.

In addition to the pore-wall dimension or parameter, the thickness of the membrane for laser light barrier functionality should be sufficient to reduce the transmission of incident laser light through the membrane by at least about 40 percent and preferably by at least 90 percent. Thus the thickness of the membrane and the cooperative solidity and complexity of the pore-walls effectively act to present a beam path long enough and complex enough to weaken or destroy the beam.

The membrane porosity as indicated is microporous, thus providing an overall pore volume equal to at least about 40 percent of the total volume of the membrane, and preferably up to about 80 percent of the total volume.

In the barrier article of the invention, the membrane can be unsupported or it can be supported on a suitable substrate such as an operating room (OR) covering material as a composite or laminate therewith. Where it is supported it can be co-extensive with its backing material or support or it may be only partly co-extensive, e.g., it may be present only in a zonal area, margin, annulus or the like such as that near or surrounding an open area intended for apposition of the membrane or backing material at the laser target operative site. If the membrane is mounted on a backing material, as for example, a woven or non-woven fabric, the membrane should face toward the beam, thus protecting the backing material. Coverings with membranes laminated to each side of a woven or non-woven fabric are also contemplated.

In another preferred aspect, the invention concerns a method of shielding personnel and equipment from a surgical laser beam of a selected wavelength. The method comprises interposing between the source of the laser beam and the personnel or equipment a protective article comprising a microporous laser beam-resistant barrier material, as described above.

In still another preferred aspect the invention concerns a surgical laser operating system. The system comprises a surgical laser capable of emitting a laser light beam having a wavelength up to about 1 micron and barrier material for portions of patients or equipment to be protected from laser light from said beam, the barrier material being as described above comprising a laser beam-resistant polymeric microporous membrane.

DETAILED DESCRIPTION OF THE EMBODIMENTS

Figure 1:
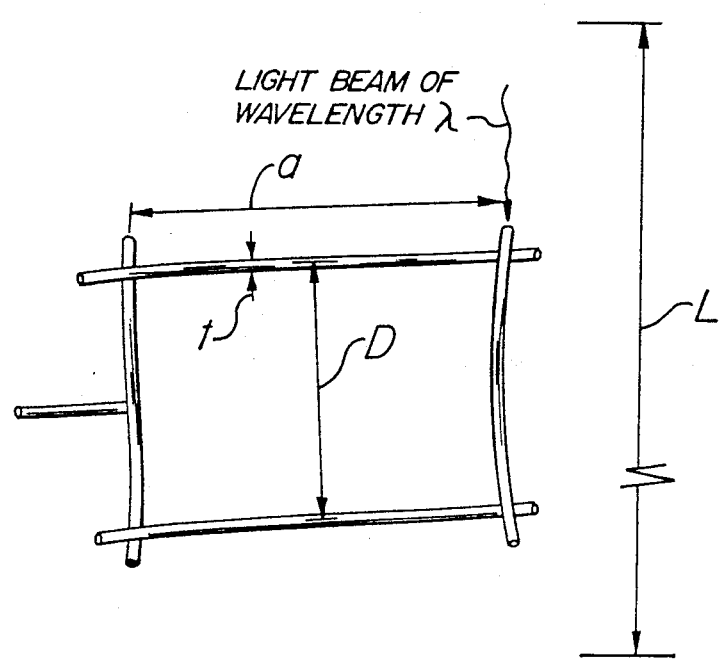
FIG. 1 is a schematic of pore-wall elements forming a single pore in an array of a plurality of such pore structures of a preferred protective barrier article of the invention.

Laser light uses the natural oscillation of atoms or molecules between energy levels to generate electromagnetic radiation which is spatially coherent. The electromagnetic radiation generated can be of a variety of spectral types such as ultraviolet, visible and infrared. Types of lasers are set forth in Table I.

TABLE 1

| Spectral Type | Type | Medium | Wavelength, nm | Radiation |
| --- | --- | --- | --- | --- |
| Ultraviolet | He—Cd | Gas | 325.0 | CW |
| | $N_2$ | Gas | 337.1 | pulsed |
| | Kr | Gas | 350.7, 356.4 | CW |
| | Ar | Gas | 351.1, 363.8 | CW, pulsed |
| Visible | He—Cd | Gas | 441.6, 537.8 | CW |
| | Ar | Gas | 457.9, 514.5 | CW, pulsed |
| | Kr | Gas | 461.9, 676.4 | CW, pulsed |
| | Xe | Gas | 460.3, 627.1 | CW |
| | Ar—Kr | Gas | 467.5, 676.4 | CW |
| | He—Ne | Gas | 632.8 | CW |
| | Ruby $Cr^{3+}AlO_3$ | Solid | 694.3 | pulsed |
| Infrared | Kr | Gas | 0.753, 0.799 × $10^3$ | CW |
| | GaAlAs | Solid (diode) | 0.850 × $10^3$ | CW |
| | GaAs | Solid (diode) | 0.904 × $10^3$ | CW |
| | Nd | Solid (glass) | 1.060 × $10^3$ | pulsed |
| | Nd | Solid (YAG) | 1.060 × $10^3$ | CW, pulsed |
| | He—Ne | Gas | 1.15, 3.39 × $10^3$ | CW |
| | $CO_2$ | Gas | 10.6 × $10^3$ | CW, pulsed |

TABLE 1-continued

| Spectral Type | Type | Medium | Wavelength, nm | Radiation |
| --- | --- | --- | --- | --- |
| | $H_2O$ | Gas | 18.0 × $10^3$ | CW, pulsed |
| | HCN | Gas | 337.0 × $10^3$ | CW, pulsed |

CW = continuous wave

To illustrate the principle of destructive interference of light, reference may be made to the condition for destructive interference of a beam of light entering a parallel planar film (such as a polymeric microporous membrane) as follows:

$$2 n d \cos \phi' = m \lambda$$

where n is the refractive index of the film, d is the thickness of the film, $\phi'$, is the angle of reflection (also equal to the angle of incidence), m = 0, 1, 2 ... is the order of the interference and $\lambda$ is the wavelength of the light beam. Jenkins & White, *Fundamentals of Optics*, 45th Ed. (New York: McGraw-Hill 1981), pp. 289–91, incorporated herein by reference. In theory, under the condition set forth above, a beam of light will undergo complete destructive interference.

In the operating room environment employing laser surgery, drapes, masks, gowns, and the like are preferably breathable, but must also serve as sterile barriers to prevent infection. Accordingly, a breathable barrier or material of a permeability which will permit the passage of air and water, yet act as a sterile barrier, must according to the invention also comprise, as indicated, a pore structure in an array which will be effective in significantly diminishing the intensity of stray light from the intended path of the laser light beam. In this respect, the area density of the wall (which is related to the porosity) and thickness of the array are cooperatively important. The area density of the wall is, in effect, the fraction of the cross-sectional area of a material transverse to the laser beam which is occupied by the solid pore-walls of the material. According to the invention, using the condition for the destructive interference of light set forth above, the functionality of the sterile barrier film materials having an effective pore-wall geometry or structure may be determined.

The functional relationship between effective pore-wall and pore structure and the wavelength of laser light is illustrated by reference to FIG. 1. FIG. 1 is a schematic illustrating a random, three-dimensional array of intersecting elements which form the solid pore-walls of a porous material where "t" is the thickness or diameter of the solid pore-walls whose magnitude ranges from about wavelength $\lambda/5$ to about wavelength $\lambda/3$; "a" is the average length of the intersecting elements between points of intersection and is variable, but not less than "D"; "L" is the total thickness of the array and is the thickness required to reduce the intensity of the laser beam, preferably to less than 10% of the original; and "D" is the average interelement center-to-center spacing and is less than 0.2 microns. Again, FIG. 1 is a schematic; the intersecting elements can be unitary, curvilinear or both as in a polymeric microporous membrane. No essential requirement exists for the elements to be rectilinear as illustrated. The light rays striking the array are partially absorbed in the solid pore-walls and undergo destructive interference. The wave entering the open space between the elements continues forward until it strikes an element with a thickness "t". Provided that the thickness "L" is sufficiently large, e.g. 5 λ, so that eventually all the light will have intersected an element of thickness "t" the beam will be completely blocked by destructive interference. However, the microporosity of the array between the parallel planar faces of the film should be such that the film membrane still has gas-permeability and bacteria-impermeability.

For purposes of illustration, the intersecting elements of FIG. 1 can be assumed to be polymeric. To balance the need for 1) permeability to the passage of air and water molecules and 2) destructive interference of stray light from the laser light beam, the following preferred conditions can be assumed for the illustrated array:

"L" is the thickness required to reduce the laser beam intensity preferably to less than 10 percent of the original;
"D" is less than about 0.2 microns;
"a" is variable but not less than "D"; and
"t" is in the range from λ/5 to λ/3.

For polymers, n can be considered as equal to 1.4 –1.6 and the angle $\phi'$ can be arbitrarily considered to be equal to 0 so that cosine 0° equals unity. It is contemplated that the porous array illustrated in FIG. 1 under the condition set forth will cause a laser beam of wavelength λ to undergo destructive interference with at least 50 percent probability.

Polymeric microporous membranes having pore sizes ranging from 0.2 to 0.45 microns have proven effective in withstanding exposure to infrared laser beams having wavelengths up to approximately 1 micron. As indicated, effective pore geometry is dependent on the thickness of the solid pore-walls or "lattice work" forming the individual pores. Consequently, an array of a plurality of individual pore structures similar to the elements illustrated in FIG. 1 (which in a preferred embodiment may comprise woven or non-woven fibers) provide an effective pore geometry, according to the invention.

Breathable barriers such as polymeric microporous membranes having pore sizes ranging from about 0.2 to about 0.45 microns are effective in withstanding exposure to infrared laser beams having wavelengths of up to about 1 micron. However, longer wavelength lasers which emit beams at wavelengths comparable to $CO_2$ lasers are strongly absorbed in the chemical bonds of almost all polymeric materials. Consequently, heat is dissipated in the chemical bonds prior to destructive interference of the light wave. Thus, there is no significant improvement in resistance to laser light emitted from lasers such as $CO_2$ lasers at least with respect to polymeric membranes.

Polymeric microporous membranes contemplated for use in the present invention include membranes such as those manufactured by phase separation due to UV polymerization. This general type of manufacture is illustrated in U.S. Pat. No. 4,466,931 incorporated herein by reference. Other contemplated polymeric microporous membranes include mixed cellulose nitrate esters, polysulfone, nylon and acrylic polymers manufactured by, for example, phase inversion or wet casting techniques, and membranes such as polytetrafluoroethylene membranes and the like made by a stretching technology (which may be conventional).

In practice, laminating or otherwise coating the barrier material on a fabric may be preferred. Polytetrafluoroethylene type membranes (0.2 micron pore size) are manufactured in a laminated form on a tricot fabric for use as drapes and gowns. However, in this context the membrane is either sandwiched between two fabrics or is on the inside adjacent to the patient's body rather than situated in the direct path of a laser light beam. Consequently, such materials would be ineffective as laser protective barriers. The practice of the present invention requires the barrier material to be situated such that the material is in the direct path of a laser light beam. Accordingly, the barrier material, when laminated or applied to a substrate, should constitute the outside of the material in the practice of the present invention.

The following examples illustrate the invention in greater detail. The examples are for the purposes of illustration only and the invention is not to be limited to the specific embodiments described in the examples. Those of ordinary skill in the art will readily recognize variations to the illustrated embodiments and all such variations are encompassed within the scope of the invention.

EXAMPLE 1

Small sections of films, fabrics and laminates described below in Table 2 were exposed to an unfocused beam of a Laser Industries pulsed $CO_2$ laser at a power output of 5 watts from a distance of approximately 20 centimeters. Where materials laminated to fabrics were tested, the non-fabric side of the material was exposed to the beam.

TABLE 2

| | | |
|---|---|---|
| 1. | "Free Repel Film" | a hydrophobic unsupported, crosslinked urethane - fluoroacrylic copolymer microporous film of nominal pore size 0.2 μm and void volume of 0.63 prepared by UV polymerization. |
| 2. | HSR Sontara | a film similar to the Free Repel Film, laminated in the production process to a polyester nonwoven fabric (Sontara TM, Dupont, U.S.A.). |
| 3. | Hydrophilic Membrane on Hollytex | a hydrophilic, crosslinked crosslinked urethane acrylate of nominal pore size 0.1 μm and void volume of 0.55, laminated in the production process to a polyester nonwoven fabric (Hollytex TM, Filtration Sciences, U.S.A.). |
| 4. | Repel Tyvek | A film similar to the Free Repel Film laminated in the production process to a polyolefine nonwoven fabric (Tyvek 1621C). |
| 5. | Sontara (Blue) 8818 | Nonwoven polyester fabric, product of Dupont, Old Hickory, Tennessee, U.S.A. used for disposable drapes and gowns. |
| 6. | Tyvek FR | A fire retardant treated polyolefine nonwoven fabric product of Dupont, U.S.A. |
| 7. | Freudenberg drape composite | Nonwoven composite of unknown polymeric material (produced by Freudenberg GmbH, Germany for use in disposable drapes and gowns). |
| 8. | Molnlycke drape composite | Paper fiber and polyethylene film laminate produced by Molnlycke, Sweden for use in disposable drapes and gowns. |

All the materials tested (of Table 2) were damaged by the $CO_2$ laser after exposure to the beam for a period of about 0.2 second.

EXAMPLE 2

Small sections of the materials described in Table 2 were exposed to a focused ND-YAG beam of a Laser Industries Sharplan 2100 Surgical Unit at powers ranging from 50 to 150 watts from a distance of approximately 20 centimeters. The results are shown below in Table 3.

Figure 2:
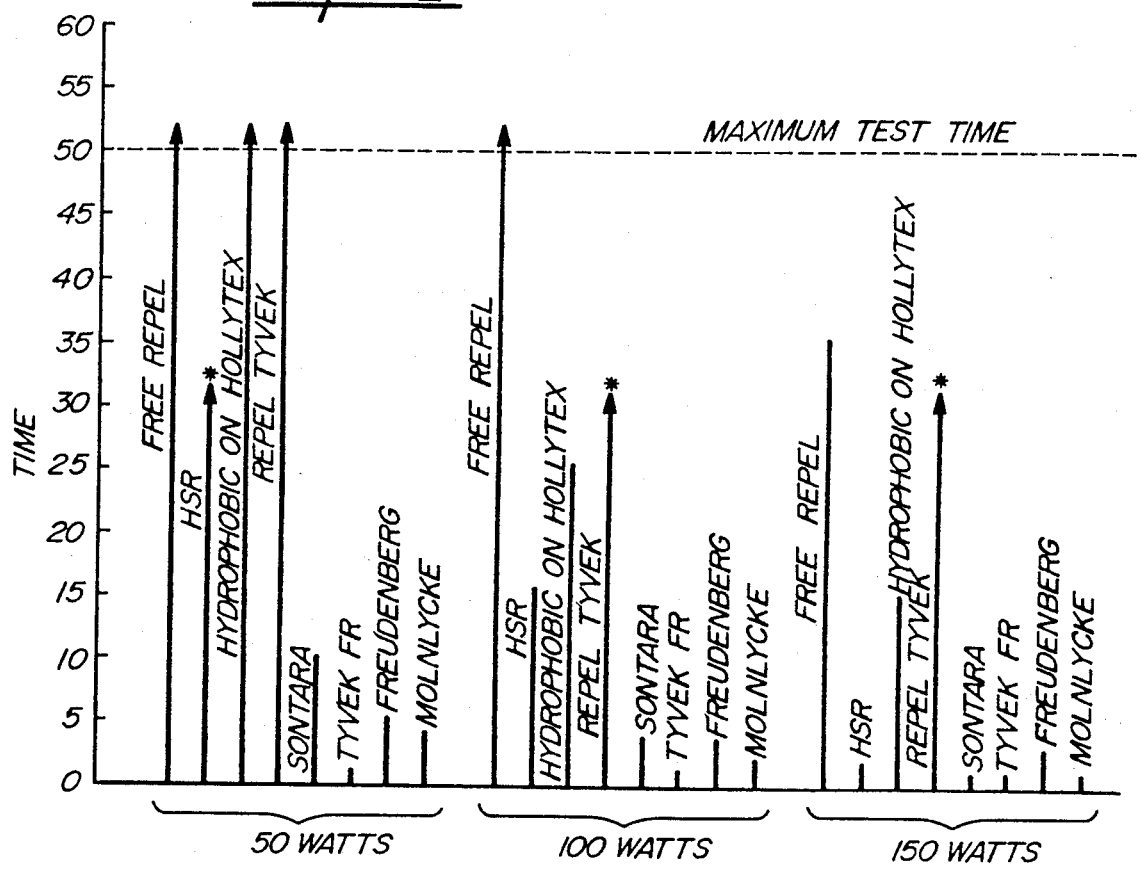
FIG. 2 is a bar graph showing the amount of exposure that various materials can stand in terms of time versus laser watts.

As indicated from the results depicted in FIG. 2, microporous membrane materials can withstand exposure to ND-YAG laser beams for 30–50 seconds. Quite surprisingly, this is an improvement of at least an order of magnitude over non-microporous membrane materials, including commercially available disposable drapes and gowns made from conventional materials.

EXAMPLE 3

Various microporous membrane materials were exposed to the ND-YAG Sharplan Laser as in Example 2 at a power of 150 watts at a distance of approximately 20 centimeters. The results are depicted in Table 3.

TABLE 3

| Membrane Polymer | Nominal Pore Size (microns) | Percent Energy Transmitted | Penetration Time |
|---|---|---|---|
| Mixed Cellulose Nitrate Esters | 0.8 | nd* | <1 second |
| Mixed Cellulose Nitrate Esters | 0.45 | 6% | >50 seconds |
| Mixed Cellulose Nitrate Esters | 0.3 | 7.5% | >50 seconds |
| Nylon | 0.2 | 15% | >50 seconds |
| Polytetrafluoroethylene | 0.45 | nd* | >50 seconds |
| Polytetrafluoroethylene | 1.0 | 40% | >50 seconds |
| Acrylic copolymer | 0.8 | 10% | 27 seconds |
| Acrylic copolymer | 5.0 | nd* | 11 seconds |

*not determined

From the series of membranes which are all made from mixed cellulose nitrate esters of different pore size, a pore size of approximately 0.2–0.5 μm is preferred.

It will be understood that while the invention has been described in its particulars with respect to preferred embodiments thereof, various changes and modifications made be made all within the full and intended scope of the claims which follow.

What is claimed is:

1. A method of shielding personnel and equipment from a surgical laser beam of a selected wavelength comprising directing said beam at a target operative site while interposing between the source of the laser beam and personnel and equipment barrier material comprising a laser beam-resistant polymeric gas-permeable and bacteria-impereable microporous membrane with solid polymeric pore-walls which provide the framework for the individual pores and having 1) membrane thickness and 2) total solid membrane pore-wall structure wherein the thickness of the walls of the pore-wall structure is equal to about one-fifth to about one-third of said wavelength such that when the membrane is interposed, the laser beam is made non-coherent and said thickness and total solid pore-wall structure cooperatively shield said personnel and equipment from at least about 40% of the light.

2. The method of claim 1 wherein the membrane thickness and pore-wall structure are such as to reduce the intensity of the laser beam to less than 10 percent of its incident intensity.

3. The method of claim 1 wherein the walls of the pore-wall structure comprise woven or non-woven fibers.

4. The method of claim 1 wherein said barrier material is in the form of a covering, drape, gown, mask or equipment cover.

5. A surgical laser operating system, comprising:
a surgical laser capable of emitting a laser light beam having a wavelength up to about 1 micron; and
barrier material for portions of patients and equipment to be protected from laser light from said beam, said barrier material comprising a laser beam-resistant polymeric gas-permeable and bacteria-impermeable micorporous membrane with solid polymeric pore-walls which provide the framework for the individual pores and having 1) membrane thickness and 2) total solid membrane pore-wall structure wherein the thickness of the walls of the pore-wall structure is equal to about one-fifthe to about one-third of said wavelength such that when the membrane is interposed, said thickness and total solid pore-wall structure cooperatively shield at least about 40% of the light.

6. The system of claim 5 wherein the membrane thickness and pore-wall structure are such as to reduce the intensity of the laser beam to less than 10 percent of its incident intensity.

7. The system of claim 5 wherein the walls of the pore-wall structure comprise woven or non-woven fibers.

8. The system of claim 5 wherein said barrier material is in the form of a covering, drape, gown, mask or equipment cover.

9. A protective barrier article for a surgical operation in cooperative employment with an incident axial laser light beam at a chosen wavelength focused on an intended or target operative site, comprising a laser beam-resistant gas-permeable and bacteria-impermeable polymeric microporous membrane with solid polymeric pore-walls which provide the frame work for the individual pores and having 1) membrane thickness and 2) total solid membrane pore-wall structure wherein the thickness of the walls of the pore-wall structure is equal to about one-fifth to about one-third of said wavelength such that when the membrane is interposed transversely of the beam said thickness and total solid pore-wall structure cooperatively shield at least about 40% of the light.

10. The article of claim 9 wherein the membrane thickness and pore-wall structure are such as to reduce the intensity of the laser beam to less than 10 percent of its incident intensity.

11. The article of claim 9 wherein the walls of the pore-wall structure comprise woven or non-woven fibers.

12. The article of claim 9 in the form of a covering, drape, gown, mask or equipment cover.

* * * * *

UNITED STATES PATENT AND TRADEMARK OFFICE
CERTIFICATE OF CORRECTION

PATENT NO. : 5,033,479

DATED : July 23, 1991

INVENTOR(S) : Tanny

It is certified that error appears in the above-identified patent and that said Letters Patent is hereby corrected as shown below:

Column 2, line 27, replace "sighificantly" with --significantly--;

Column 4, line 17, replace "∅', is" with --∅' is--;

Column 7, line 57, replace "bacteria-impereable" with --bacteria-impermeable--;

Column 8, line 27, replace "one-fifthe" with --one-fifth--;

Column 8, line 45, replace "bacteria-impremeable" with --bacteria-impermeable--.

Signed and Sealed this

Ninth Day of March, 1993

*Attest:*

STEPHEN G. KUNIN

*Attesting Officer*     *Acting Commissioner of Patents and Trademarks*